US009089321B2

(12) United States Patent
Snyder et al.

(10) Patent No.: US 9,089,321 B2
(45) Date of Patent: Jul. 28, 2015

(54) WHEELED SUTURE PASSER

(71) Applicant: Biomet Sports Medicine, LLC, Warsaw, IN (US)

(72) Inventors: Terry H. Snyder, North Webster, IN (US); Daniel D. Fritzinger, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 257 days.

(21) Appl. No.: 13/652,003

(22) Filed: Oct. 15, 2012

(65) Prior Publication Data
US 2014/0107673 A1 Apr. 17, 2014

(51) Int. Cl.
A61B 17/04 (2006.01)

(52) U.S. Cl.
CPC ......... *A61B 17/0469* (2013.01); *A61B 17/0483* (2013.01); *A61B 17/0485* (2013.01)

(58) Field of Classification Search
CPC ............... A61B 17/04; A61B 17/0483; A61B 17/06061; A61B 17/0469; A61B 17/0485
USPC .................................. 606/104, 148, 216, 232
See application file for complete search history.

(56) References Cited

U.S. PATENT DOCUMENTS

| 2,959,172 | A | 11/1960 | Held |
| 4,890,615 | A | 1/1990 | Caspari et al. |
| 4,923,461 | A | 5/1990 | Caspari et al. |
| 5,281,237 | A | 1/1994 | Gimpelson |
| 5,439,467 | A | 8/1995 | Benderev et al. |
| 5,562,683 | A | 10/1996 | Chan |
| 5,562,687 | A | 10/1996 | Chan |
| 5,676,675 | A | 10/1997 | Grice |
| 5,776,151 | A | 7/1998 | Chan |
| 5,810,848 | A | 9/1998 | Hayhurst |
| 5,830,231 | A | 11/1998 | Geiges, Jr. |
| 5,993,466 | A | 11/1999 | Yoon |
| 6,206,893 | B1 | 3/2001 | Klein et al. |
| 6,629,984 | B1 | 10/2003 | Chan |
| 7,004,951 | B2 | 2/2006 | Gibbens, III |
| 8,303,604 | B2 | 11/2012 | Stone et al. |
| 8,490,713 | B2 | 7/2013 | Furnish et al. |
| 8,636,752 | B2 | 1/2014 | Cabrera et al. |
| 8,679,135 | B2 | 3/2014 | Stone et al. |
| 8,696,688 | B2 | 4/2014 | Stone |

(Continued)

OTHER PUBLICATIONS

EZPass Suture Passers. Biomet Sports Medicine. (2014) 2 pages.
Shoulder Arthroscopy. Bioraptor? Curved Osteoraptor? Curved Suture Anchors and Guide System. Smith & Nephew. (2011). pp. 1-53.

(Continued)

*Primary Examiner* — Victor Nguyen
(74) *Attorney, Agent, or Firm* — Harness, Dickey

(57) ABSTRACT

A suture passer assembly is used for manipulating a suture with a selectively moveable wire member. The suture passer assembly includes at least one grasping member and a single-body hollow tube. The tube defines a first end, a second end, a tube wall, and a tube passage extending from the first end to the second end. The wire member is moveably received within the tube passage. The tube wall includes at least one aperture that is disposed between the first end and the second end. A first portion of the grasping member extends through the tube wall and into the tube passage via the aperture. A second portion of the grasping member remains outside the hollow tube. The first portion is operable to grasp the wire member and selectively move the wire member relative to the hollow tube due to manipulation of the second portion of the grasping member.

22 Claims, 6 Drawing Sheets

(56) References Cited

U.S. PATENT DOCUMENTS

| | | |
|---|---|---|
| 8,709,022 B2 | 4/2014 | Stone et al. |
| 2005/0080476 A1* | 4/2005 | Gunderson et al. .......... 623/1.11 |
| 2009/0018553 A1 | 1/2009 | McLean et al. |
| 2011/0202074 A1 | 8/2011 | Talmo et al. |
| 2012/0059396 A1 | 3/2012 | Harris et al. |
| 2012/0123448 A1 | 5/2012 | Flom et al. |
| 2012/0143224 A1 | 6/2012 | Chan |
| 2013/0116710 A1 | 5/2013 | Ziniti et al. |

OTHER PUBLICATIONS

SpeedPass™ Suture Retrievers. Arthrotek® a Biomet Company brochure. (2004). 2 pages.

The Material Difference. Biomet® Sports Medicine. (2008). pp. 1-12.

The Next Generation in Shoulder & Elbow Repair and Reconstruction Technology. Arthrex® brochure. (2014) pp. 1-55.

* cited by examiner

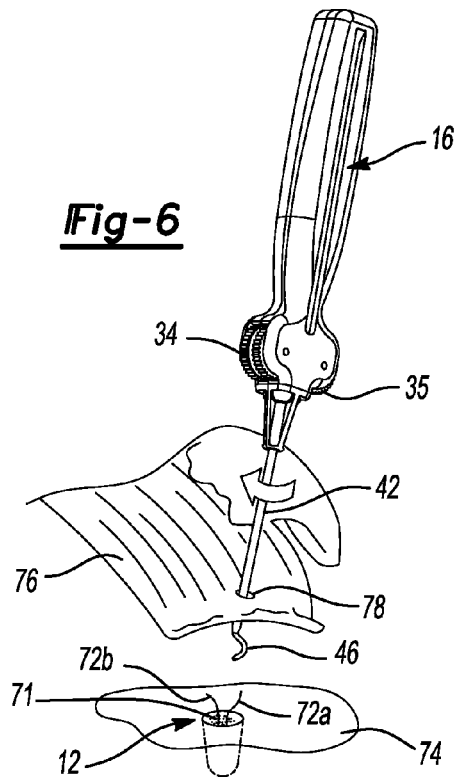
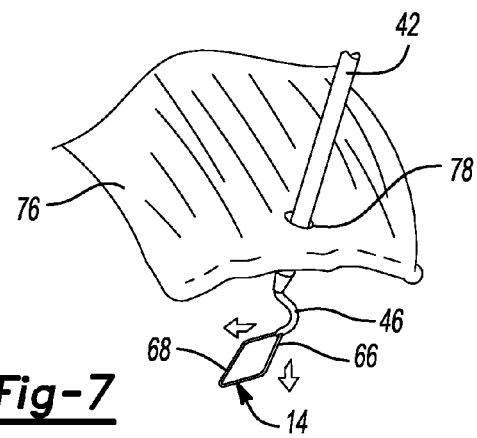
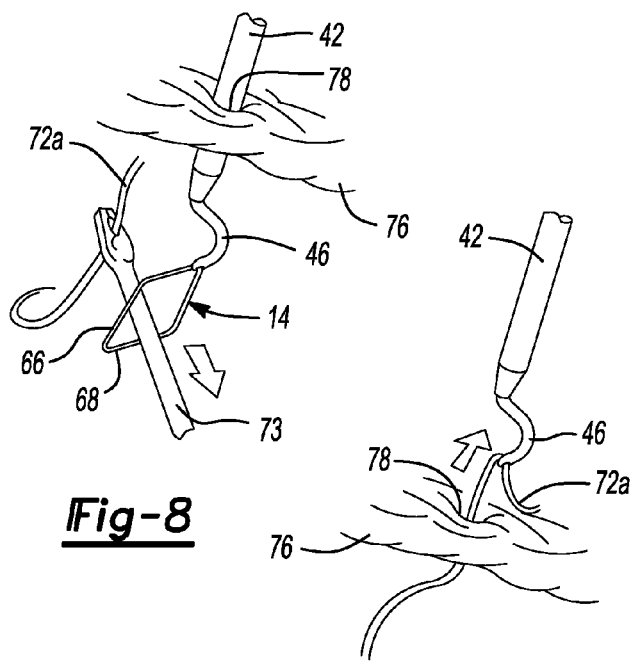
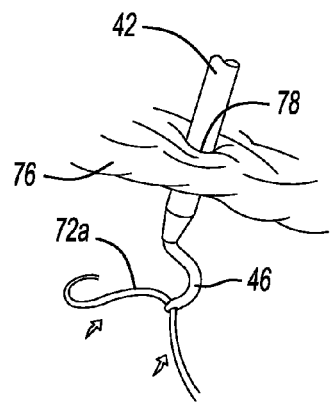

WHEELED SUTURE PASSER

FIELD

The present disclosure relates to a wheeled suture passer and, more particularly, to a wheeled suture passer for securely advancing a wire for use as a suture retrieve or other appropriate use.

BACKGROUND

This section provides background information related to the present disclosure which is not necessarily prior art.

Damaged anatomical tissue can be repaired using sutures. A typical suture can be threaded through two separate areas of tissue, and the suture can be tied to thereby attach the areas of tissue. As such, the areas of tissue can be held together by the suture and, over time, the areas of tissue can heal together to restore function of the anatomy. These procedures can be used for various surgical procedures, such as repair of a torn rotator cuff, etc.

Threading the suture through tissue and then tying a knot in the suture can be difficult, especially when the procedure is performed arthroscopically. This is because the surgeon's view of the area can be limited, because there can be relatively little open space within the anatomy to work, etc. Thus, various suture passers have been proposed for facilitating these procedures.

SUMMARY

This section provides a general summary of the disclosure, and is not a comprehensive disclosure of its full scope or all of its features.

A suture passer assembly is disclosed that is used for manipulating a suture with a selectively moveable wire member. The suture passer assembly includes at least one grasping member and a single-body hollow tube. The tube defines a first end, a second end, a tube wall, and a tube passage extending from the first end to the second end. The wire member is moveably received within the tube passage. The tube wall includes at least one aperture that is disposed between the first end and the second end. A first portion of the grasping member extends through the tube wall and into the tube passage via the aperture. A second portion of the grasping member remains outside the hollow tube. The first portion is operable to grasp the wire member and selectively move the wire member relative to the hollow tube due to manipulation of the second portion of the grasping member.

Moreover, a method of selectively moving a portion of a suture from a first anatomical location to a second anatomical location is disclosed. The method includes inserting a hollow tube of a suture passer assembly into a patient toward the first anatomical location and toward the portion of the suture. The hollow tube is a single body defining a first end, a second end, a tube wall, and a tube passage extending from the first end to the second end. A wire member with a gripping end is moveably received within the tube passage. The tube wall includes at least one aperture that is disposed between the first end and the second end. The suture passer assembly also includes at least one grasping member with a first portion extending through the tube wall and into the tube passage via the at least one aperture. A second portion of the at least one grasping member remains outside the hollow tube. Additionally, the method includes manipulating the second portion such that the first portion pushes the gripping end of the wire member out of the hollow tube from the second end. Furthermore, the method includes manipulating the second portion such that the first portion pulls the gripping end and the portion of the suture toward the hollow tube to secure the portion of the suture to the suture passer assembly. Moreover, the method includes moving the portion of the suture to the second anatomical location using the suture passer assembly.

Still further, a suture passer assembly for manipulating a suture is disclosed. The suture passer assembly includes a wire member. The assembly also includes a handle member with a handle passage defined therethrough and a first wheel and a second wheel that are each rotatably supported on the handle member. Additionally, the assembly includes a single-body hollow tube defining a longitudinal axis, a first end, a second end, a tube wall, and a tube passage extending from the first end to the second end. The hollow tube is received within the handle passage, and the wire member is moveably received within the tube passage. The tube wall includes a first slot and a second slot that are each disposed between the first end and the second end and that are disposed on opposite sides of the longitudinal axis. The first wheel partially extends through the first aperture and into the hollow tube, and the second wheel partially extends through the second aperture and into the hollow tube. The first and second wheels are operable to cooperatively grasp the wire member within the tube passage such that driving rotation of at least one of the first wheel and the second wheel advances the wire member relative to the tube member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 6-10 are isometric views of the suture passer of FIG. 1 shown being used to pass a suture through anatomical tissue.

Corresponding reference numerals indicate corresponding parts throughout the several views of the drawings.

DETAILED DESCRIPTION

Example embodiments will now be described more fully with reference to the accompanying drawings.

Figure 1:
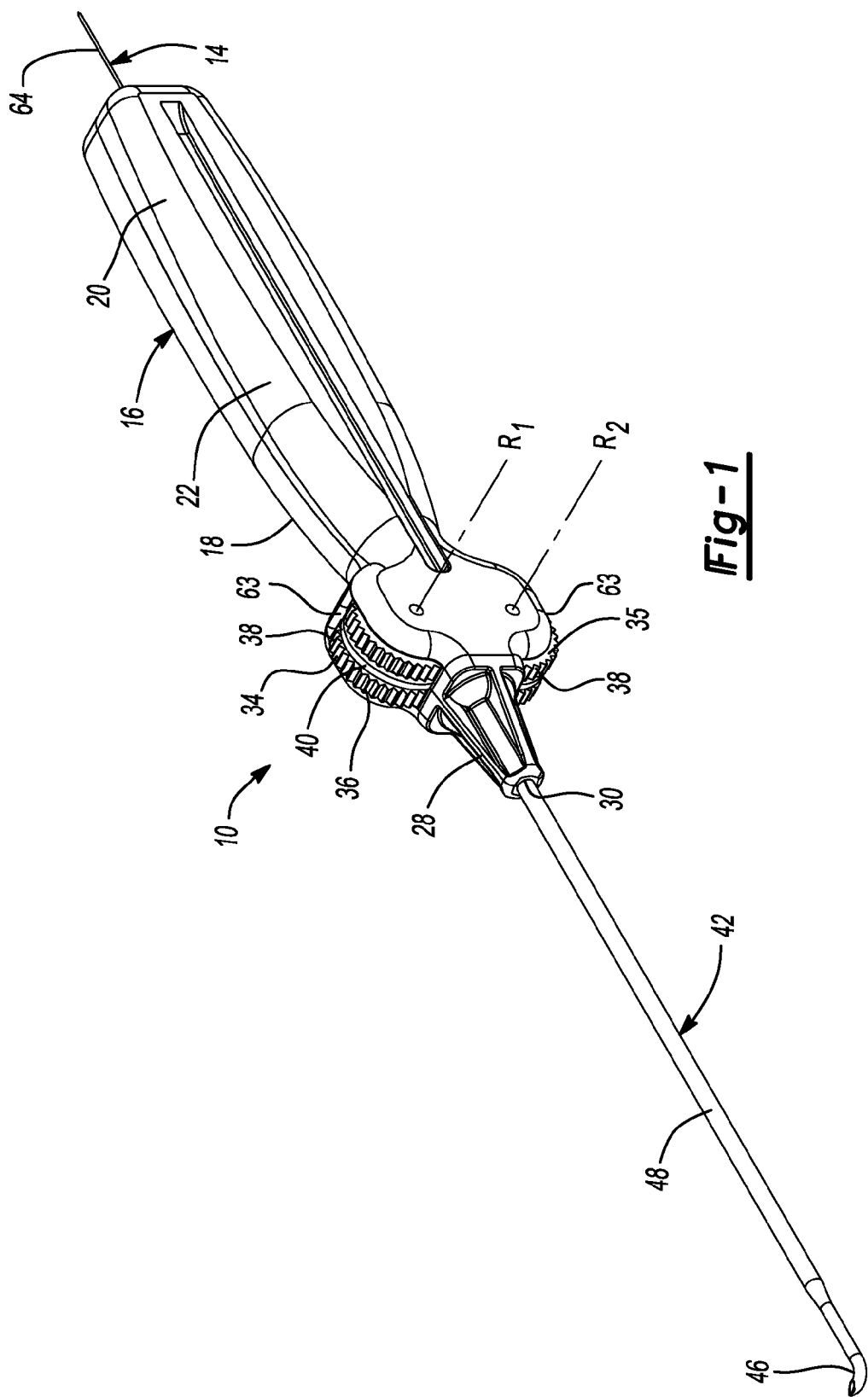
FIG. 1 is an isometric view of a suture passer illustrated according to various exemplary embodiments of the present disclosure.
Figure 2:
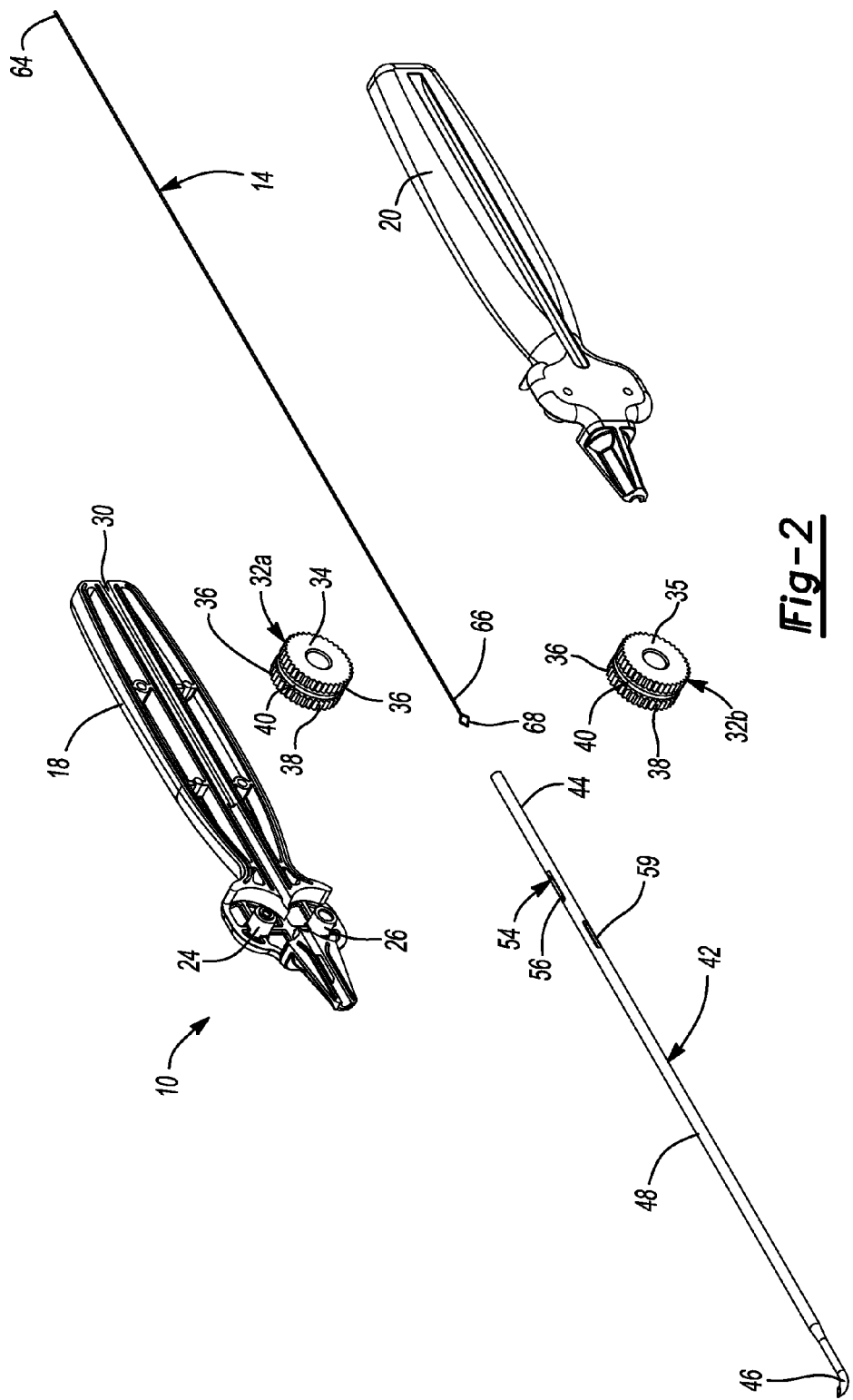
FIG. 2 is an exploded view of the suture passer of FIG. 1.

Referring initially to FIGS. 1 and 2, a suture passer assembly 10 is illustrated according to various exemplary embodiments of the present disclosure. As will be discussed, the suture passer assembly 10 can be used for manipulating a suture 12 (FIGS. 6-10). More specifically, a wire member 14 (FIGS. 7 and 8) can be moveably mounted within the suture passer assembly 10, and the suture passer assembly 10 can be used to selectively move the wire member 14 for manipulating the suture 12 (e.g., for passing the suture 12 through anatomical tissue) as will be discussed in greater detail below.

Figure 4:
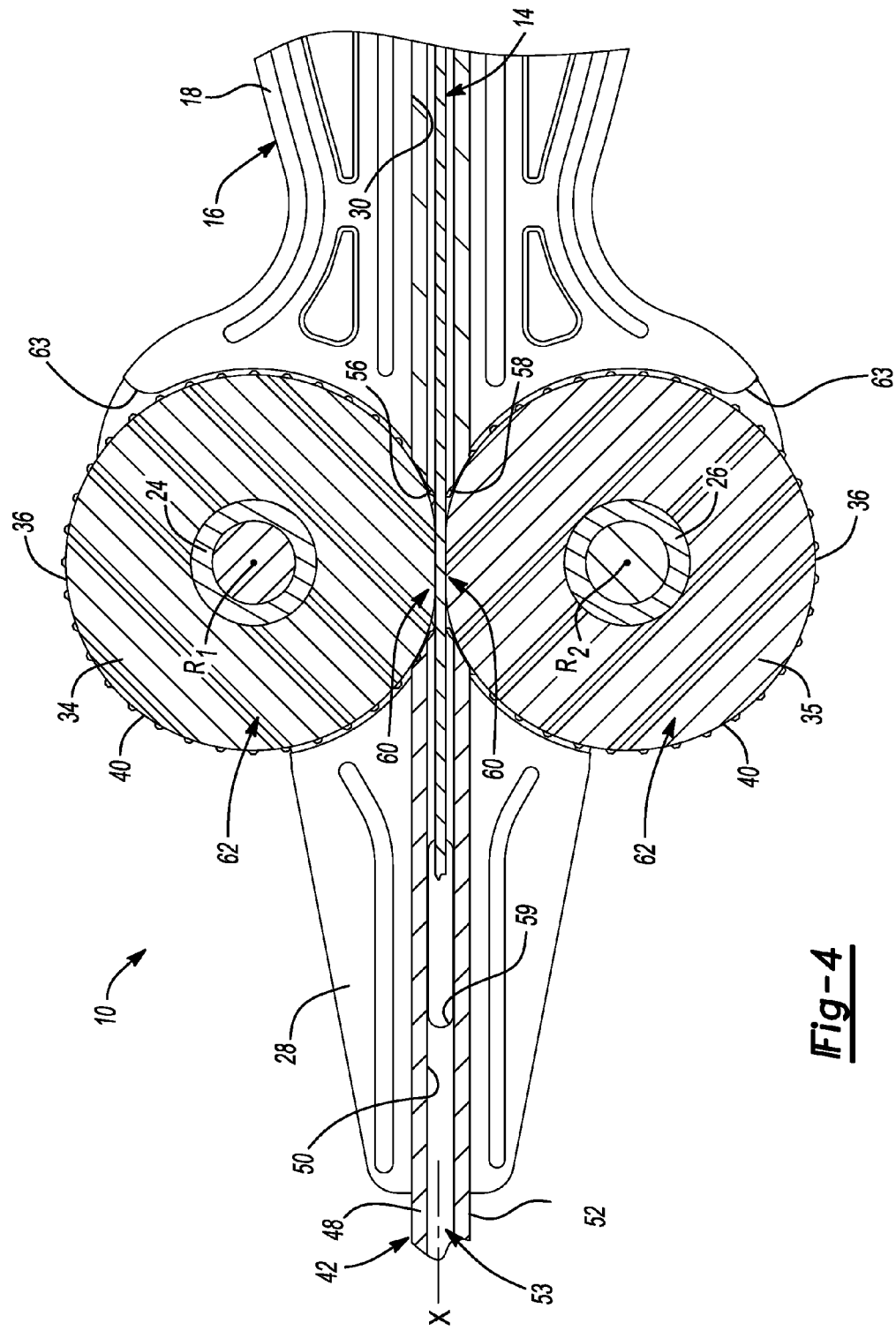
FIG. 4 is a longitudinal sectional view of the suture passer of FIG. 1.

As shown in FIGS. 1 and 2, the suture passer assembly 10 can include a handle member 16. The handle member 16 can include a first portion 18 and a second portion 20 that are joined together in a clam-shell or other type of configuration. The handle member 16 can be made of a polymeric or other type of material. The first and second portions 18, 20 can cooperate to define a handle end 22 of the handle member 16, which the user (e.g., a surgeon) can comfortably hold in one hand. The first and second portions 18, 20 can also cooperate to define a lead end 28 of the handle member 16. The lead end 28 can be frustoconical in shape and can be disposed on an opposite end of the handle member 16 from the handle end 22. Moreover, one or both of the first and second portions 18, 20 can also define a first hub 24 and a second hub 26 (FIG. 2). The hubs 24, 26 can be cylindrical and can extend perpendicularly between the first and second portions 18, 20, within the handle member 16. Additionally, the handle member 16 can define a handle passage 30 (FIG. 4) that extends longitudinally therethrough along an axis X. As shown in FIG. 4, the wire member 14 can be moveably received within the handle passage 30.

The suture passer assembly 10 can also include at least one grasping member 32a, 32b that are operable to selectively grasp and advance the wire member 14 relative to the handle member 16 and other portions of the assembly 10. In the embodiments illustrated, there are two grasping members 32a, 32b that are embodied as a first wheel 34 and a second wheel 35, respectively. However, it will be appreciated that there could be a single grasping member 32a, 32b or any other number of grasping members 32a, 32b without departing from the scope of the present disclosure. Moreover, the grasping members 32a, 32b could be embodied in ways other than the wheels 34, 35 (e.g., such as levers, sliders, etc.) without departing from the scope of the present disclosure.

Figure 5:
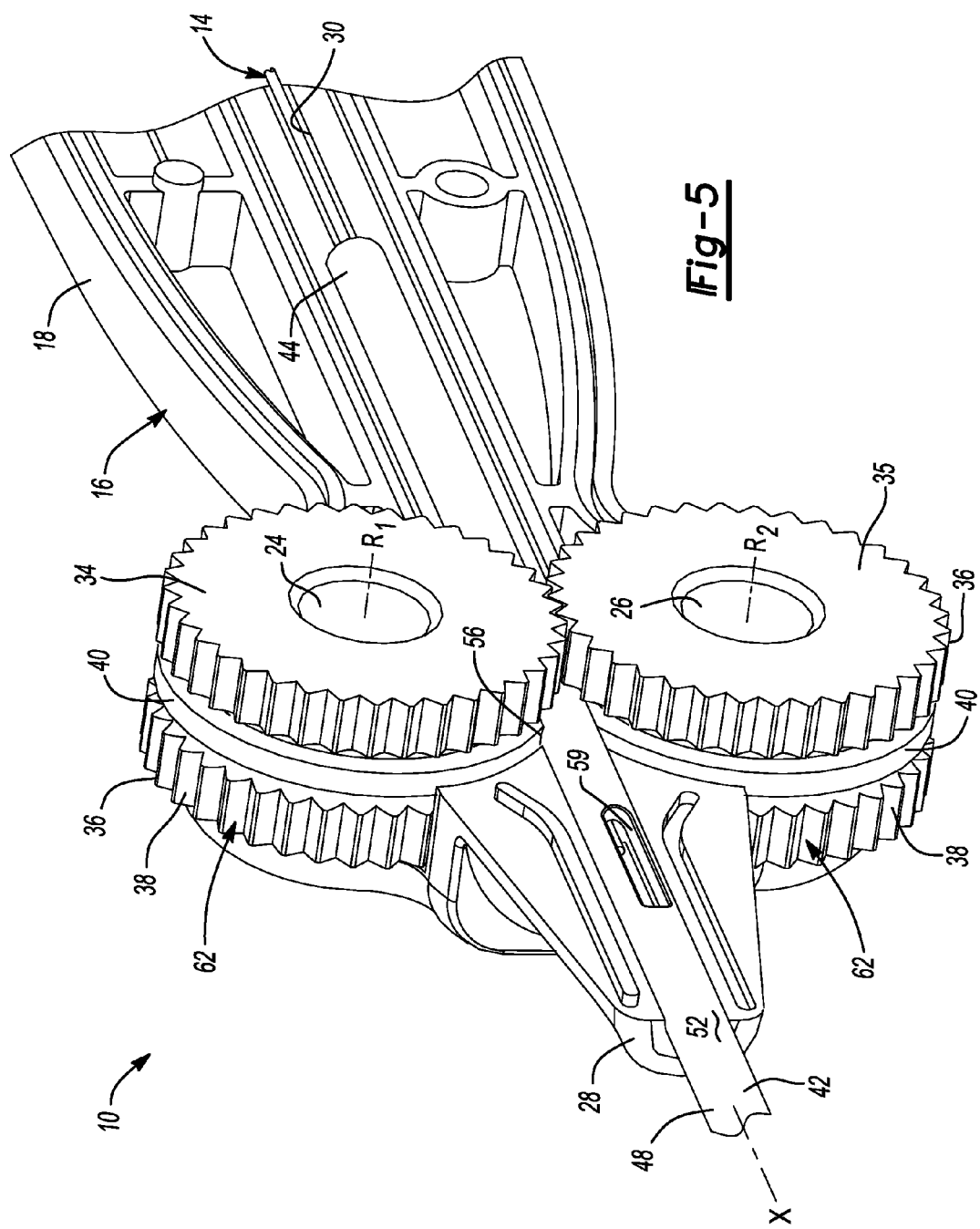
FIG. 5 is an isometric view of the suture passer of FIG. 1, wherein a portion of a handle member has been removed.

The wheels 34, 35 can both be cylindrical and can both include an outer diameter surface 36. Also, the outer diameter surface 36 can be defined by sets of teeth 38 (cogs, radial projections, etc.). The teeth 38 can have a generally triangular profile as shown in FIG. 5, but the teeth 38 can have any suitable grippable or engageable shape. The outer diameter surface 36 can also be defined by a compressible member 40 of the respective wheel 34, 35. The compressible member 40 can be made from a compressible, but relatively high friction material, such as rubber, foam, etc. However, the member 40 can be substantially incompressible and rigid in some embodiments as well. Also, in the embodiments shown in FIG. 5, the compressible member 40 can be an annular band that is disposed longitudinally between the sets of teeth 38 of the respective wheel 34, 35.

The wheels 34, 35 can be rotationally supported on the hubs 24, 26, respectively (FIG. 4). As such, the wheels 34, 35 can rotate about respective rotational axes R1, R2 relative to the handle member 16.

As will be discussed, the compressible member 40 can abut and frictionally engage the wire member 14. Thus, rotation of the wheels 34, 35 about the axes R1, R2 can advance (i.e., push or pull) the wire member 14 within the assembly 10.

Also, the wheels 34, 35 can be mounted such that the set of teeth 38 of the first wheel 34 can meshingly engage the set of teeth 38 of the second wheel 35. Accordingly, the user can drivingly rotate only one wheel 34, 35 to thereby drivingly rotate the other wheel 34, 35 for added convenience and improved ergonomics.

It will be appreciated that the outer diameter surface 36 can include radial projections having shapes, spacing, etc. other than those of the illustrated teeth 38 for meshingly engaging the wheels 34, 35. Additionally, in some embodiments, the outer diameter surfaces 36 can be smooth such that the wheels 34, 35 do not meshingly engage. Otherwise, in some embodiments, the outer diameter surfaces 36 can be smooth and can frictionally engage each other so that the wheels 34, 35 can rotatably drive each other.

Figure 3:
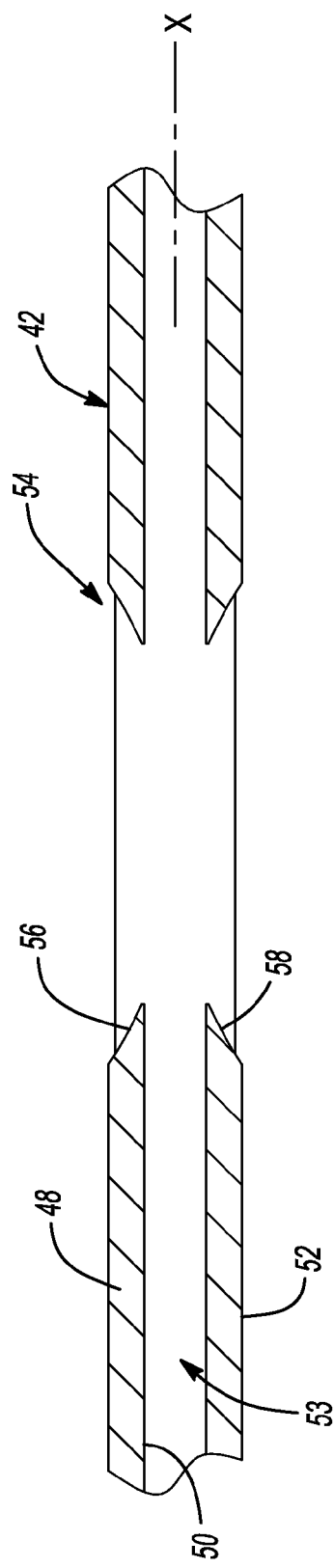
FIG. 3 is a longitudinal sectional view of a tube of the suture passer of FIG. 1.

Furthermore, the assembly 10 can include a hollow tube 42. The hollow tube 42 can be a monolithic body (i.e., single body, uni-body construction, etc.). The tube 42 can be constructed from metal or polymer. The tube 42 can also extend along the longitudinal axis X. As shown in FIGS. 2 and 3, the tube 42 can define a first end 44, a second end 46, and a tube wall 48. The first end 44 and much of the second end 46 can be axially straight; however, terminal portions of the second end 46 can axially curve as shown in FIGS. 1 and 2. The second end 46 can also include sharpened edges such that the second end 46 can be used for cutting anatomical tissue as will be discussed.

The tube wall 48 can define an inner tube surface 50 and an outer tube surface 52 as shown in FIG. 3. Moreover, a tube passage 53 can extend longitudinally along the axis X through the tube 42. The tube passage 53 can extend continuously along the tube 42 between the first end 44 and the second end 46. As will be discussed, the wire member 14 can be moveably received within the tube passage 53.

The tube 42 can be fixedly attached and supported by the handle member 16. More specifically, the first and second portions 18, 20 of the handle member 16 can be attached such that the first end 44 of the tube 42 is enclosed within the handle passage 30 and sandwiched between the first and second portions 18, 20 of the handle member 16. As shown in FIGS. 2 and 4, the tube wall 48 can include one or more orientation openings 59 (e.g., slots) that receive complementary projections of the first and/or second portions 18, 20 for further securing the tube 42 to the handle member 16. Adhesives, fasteners, or other means can additionally be used for securing the tube 42 to the handle member 16. With the first end 44 secured to the handle member 16, the second end 46 of the tube 42 can extend out from and can be exposed from the handle member 16.

As shown in FIGS. 2-5, the tube wall 48 can include at least one aperture 54. The aperture 54 can be disposed between the first and second ends 44, 46 of the tube 42. In the embodiments illustrated in FIGS. 3 and 4, the tube wall 48 includes two apertures 54 that are embodied as respective elongate slots 56, 58. The slots 56, 58 can extend radially through both the inner tube surface 50 and the outer tube surface 52. Also, the slots 56, 58 can extend substantially parallel to the axis X and can be disposed symmetrically on opposite sides of the axis X. As shown in FIG. 3, the slots 56, 58 can taper outward from the inner tube surface 50 to the outer tube surface 52. However, it will be appreciated that the tube 42 can include any number of apertures 54, and the aperture(s) 54 can have any suitable shape and any suitable position on the tube wall 48.

As shown in FIG. 4, a first portion 60 of each wheel 34, 35 can be received within the slots 56, 58, respectively. Specifically, the first portion 60 is defined at an inner radial segment of the compressible member 40 as the wheels 34, 35 rotate. These first portions 60 extend through the tube wall 48 and radially into the tube passage 53 via the respective slot 56, 58. The slots 56, 58 can be shaped and sized such that the first portion 60 substantially fills the entire respective slot 56, 58. The remaining portions (i.e., second portions 62) remain outside the tube 42. The second portion 62 can be defined on the outer radial portions of the compressible members 40.

Also, each of the sets of teeth 38 can remain outside the tube 42 because the teeth 38 are spaced away on either side of the respective compressible members 40 (along the respective rotational axis R1, R2). Also, the handle member 16 can include openings 63 (FIGS. 1 and 4) that partially expose the respective second portions 62 of the wheels 34, 35 so that the user can contact the wheels 34, 35.

As shown in FIG. 2, the wire member 14 can be a continuous, flexible wire having a proximal end 64 and a distal end 66. The wire member 14 can be made from Nitinol, a polymer or other suitable material. The distal end 66 can include a diamond-shaped loop 68. The loop 68 can be resiliently compressible. Also, in some embodiments, the distal end 66 can include opposed pinchers, a hook, or other devices. The wire member 14 can be moveably received within the handle passage 30 and the tube passage 53. Specifically, to load the wire member 14, the wire member 14 can be inserted into the handle passage 30 defined by the handle end 22 and advanced along the axis X toward the tube 42. Since the tube passage 53 is coaxial with the handle passage 30, the wire member 14 can advance easily into the first end 44 of the tube 42 and advance between the wheels 34, 35 as shown in FIG. 4. Then, the wheels 34, 35 can be rotated to further advance the distal end 66 toward the second end 46 of the tube 42.

It will be appreciated that the distal end 66 of the wire member 14 can be relatively easily and conveniently advanced toward the second end 46 of the tube 42. This is because the tube 42 is monolithic (i.e., single body, uni-body, etc.), because the opening 59 is blocked by the handle member 16, and because the slots 56, 58 are blocked by the first portions 60 of the wheels 34, 35. As such, the wire member 14 has little or no ability to advance out of the tube 42 until the distal end 66 reaches the second end 46 of the tube 42. Accordingly, the suture passer assembly 10 can be prepared for use relatively quickly and conveniently.

Moreover, once the wire member 14 is loaded within the assembly 10, the loop 68 can be selectively advanced out and retracted into the second end 46 of the tube 42. This can be accomplished by drivingly rotating the wheels 34, 35. As mentioned above, the user can apply force to only one wheel 34, 35 and because the wheels 34, 35 are meshingly engaged, both wheels 34, 35 can advance the wire member 14 for added convenience.

FIGS. 6-10 illustrate exemplary uses of the suture passer assembly 10. In some embodiments, the suture passer assembly 10 can be used to repair a damaged rotator cuff; however, it will be appreciated that the suture passer assembly 10 can be used for repairing any anatomical feature. Also, the assembly 10 can be used arthroscopically in some embodiments.

As shown in FIG. 6, the suture 12 can include an anchor 71 that can be anchored (e.g., threaded) into a first anatomical feature 74 (e.g., bone tissue). The suture 12 can also include two flexible ties 72a, 72b that extend from the anchor. Thus, one or more incisions (not shown) can be made in the patient's skin, and the anchor 71 can be fixed to the first anatomical feature 74. The ties 72a, 72b can be initially untied as shown in FIG. 6.

Next, an opening, such as a piercing or an incision 78 can be made in a second anatomical feature 76 (e.g., soft tissue such as a torn rotator cuff). The incision 78 can be in communication with one or more other incisions formed within the patient's skin. The incision 78 can be made directly by the sharpened edges of the second end 46 of the tube 42. Alternatively, the incision 78 can be made using another cutting tool. Also, a cannula (not shown) can be inserted into the incision 78 and the second end 46 of the tube 42 can be advanced through the incision 78 via the cannula.

Once the second end 46 has been inserted through the incision 78 (FIGS. 6 and 7), the wheels 34, 35 can be rotated in a first direction to advance the loop 68 out of the second end 46 (FIG. 7). The loop 68 can bias open to a width that is larger than that of the second end 46.

Then, as shown in FIG. 8, a tool 73 can be inserted into the patient (e.g., through an incision that is not shown), and the tool 73 can be used to grab one of the ties 72a and advance the tie 72a into the loop 68 as indicated by the arrow in FIG. 8.

Once the tie 72a has been received in the loop 68, the wheels 34, 35 of the suture passer assembly 10 can be rotated in a second direction to retract the loop 68 back into the second end 46. Specifically, as the loop 68 retracts, the loop 68 can resiliently flex to close around the tie 72a. Thus, the tie 72a can be restrained and captured within the loop 68 and/or restrained between the loop 68 and the inner tube surface 50 of the tube 42 as shown in FIG. 9.

Once the tie 72a is restrained, the surgeon can pull the assembly 10 back through the incision 78, thereby pulling the tie 72 through the incision. Subsequently, the ties 72a, 72b can be tied in one or more conventional knots to thereby attach the first and second anatomical features 74, 76 together.

Accordingly, the suture passer assembly 10 can allow the user to conveniently load the wire member 14 therein. Also, the suture passer assembly 10 can allow the user to comfortably and accurately control advancement of the wire member 14 within the tube 42. As a result, the user can more quickly and efficiently perform surgical procedures using sutures 12.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture passer assembly for manipulating a suture with a selectively moveable wire member, the suture passer assembly comprising:
    at least one grasping member; and
    a single-body hollow tube having a tube wall extending from a first end to a second end and defining a tube passage extending from the first end to the second end, the wire member moveably received within the tube passage, the tube wall including at least one aperture extending through the tube wall to the tube passage that is disposed between the first end and the second end, a first portion of the at least one grasping member extending through the tube wall and into the tube passage via the at least one aperture, a second portion of the at least one grasping member remaining outside the hollow tube, the first portion operable to grasp the wire member and selectively move the wire member relative to the hollow tube due to manipulation of the second portion of the at least one grasping member.

2. The suture passer assembly of claim 1, further comprising a handle member, the handle moveably supporting the at least one grasping member and operably supporting the hollow tube.

3. The suture passer assembly of claim 1, wherein the handle member encloses the first end of the hollow tube and wherein the second end of the hollow tube is exposed from the handle member.

4. The suture passer assembly of claim 1, wherein the at least one grasping member comprises a first grasping member and a second grasping member, wherein the at least one aperture comprises a first aperture and an opposed second aperture extending through the tube wall to the tube passage, wherein the first grasping member is received within the first aperture and the second grasping member is received within the opposed second aperture, the first and second grasping members being operable to cooperatively and selectively move the wire member relative to the hollow tube.

5. The suture passer assembly of claim 4, wherein the hollow tube defines a longitudinal axis, and wherein the first aperture and the second aperture are substantially symmetrical with respect to each other on opposites sides of the longitudinal axis.

6. The suture passer assembly of claim 1, wherein the at least one grasping member includes a wheel that is rotationally supported relative to the hollow tube.

7. The suture passer assembly of claim 6, wherein the wheel includes a compressible member, the compressible member being received within the at least one aperture.

8. The suture passer assembly of claim 1, wherein the at least one grasping member includes a first wheel and a second wheel that cooperate to selectively move the wire member relative to the hollow tube, the first wheel including a first set of radial projections, the second wheel including a second set of radial projections, the first and second sets of radial projections being configured to cooperatively engage one another such that rotation of one of the first and second wheels drives the other of the first and second wheels.

9. The suture passer assembly of claim 8, wherein the first wheel is operable to rotate about a first rotational axis and the second wheel is operable to rotate about a second rotational axis, the first portion of the first wheel being spaced away from the first set of radial projections along the first rotational axis, the first portion of the second wheel being spaced away from the second set of radial projections along the second rotational axis, the first and second set of radial projections being disposed outside the hollow tube.

10. The suture passer assembly of claim 1, wherein the hollow tube defines a longitudinal axis, and wherein the at least one aperture is a slot that extends longitudinally substantially parallel to the longitudinal axis.

11. The suture passer assembly of claim 10, wherein the tube wall includes an outer tube surface and an inner tube surface, wherein the slot tapers outward from the inner tube surface to the outer tube surface.

12. The suture passer assembly of claim 1, further comprising the wire member.

13. A suture passer assembly for manipulating a suture with a selectively moveable wire member, the suture passer assembly comprising:
at least one grasping member; and
a single-body hollow tube having a tube wall extending from a first end to a second end and defining a tube passage extending from the first end to the second end, the wire member moveably received within the tube passage, the tube wall including at least one aperture extending through the tube wall to the tube passage that is disposed between the first end and the second end, a first portion of the at least one grasping member extending through the tube wall and into the tube passage via the at least one aperture, a second portion of the at least one grasping member remaining outside the hollow tube, the first portion operable to grasp the wire member and selectively move the wire member relative to the hollow tube due to manipulation of the second portion of the at least one grasping member, wherein the hollow tube is curved at the second end, and wherein the second end includes a sharpened edge.

14. A suture passer assembly for manipulating a suture, the suture passer assembly comprising:
a wire member;
a grasping member having a first wheel and a second wheel that are each rotatable; and
a single-body hollow tube having a tube wall that extends substantially along a longitudinal axis from a first end to a second end and defining a tube passage extending from the first end to the second end, the wire member moveably received within the tube passage, the tube wall including a first slot and a second slot that are each disposed between the first end and the second end and that are disposed on opposite sides of the longitudinal axis, each slot extending through the tube wall to the tube passage, the first wheel partially extending through the first slot and into the hollow tube, the second wheel partially extending through the second slot and into the hollow tube, the first and second wheels operable to cooperatively grasp the wire member within the tube passage such that driving rotation of at least one of the first wheel and the second wheel advances the wire member relative to the tube.

15. The suture passer assembly of claim 14, wherein the first wheel includes a first set of radial projections, wherein the second wheel includes a second set of radial projections, and the first and second sets of radial projections are meshingly engaged such that rotation of one of the first and second wheels rotatably drives the other of the first and second wheels.

16. The suture passer assembly of claim 14, wherein both the first and second wheels includes a compressible member that resiliently compresses radially when grasping the wire member.

17. The suture passer assembly of claim 14, wherein the first slot and first wheel are disposed substantially symmetrically about the longitudinal axis relative to the second slot and the second wheel.

18. The suture passer assembly of claim 14, wherein the tube wall includes an outer tube surface and an inner tube surface, wherein the first slot tapers outward from the inner tube surface to the outer tube surface, and wherein the second slot tapers outward from the inner tube surface to the outer tube surface.

19. The suture passer assembly of claim 14, further comprising a handle member, the handle member movably supporting the first wheel and the second wheel relative to the hollow tube.

20. The suture passer assembly of claim 19, wherein the handle member encloses the first end of the hollow tube and wherein the second end of the hollow tube is exposed from the handle member.

21. The suture passer assembly of claim 14, wherein the hollow tube is curved at the second end, and wherein the second end includes a sharpened edge.

22. The suture passer assembly of claim 14, wherein the first wheel is operable to rotate about a first rotational axis and the second wheel is operable to rotate about a second rotational axis, a portion of the first wheel partially extending through the first slot being spaced away from the first set of radial projections along the first rotational axis, a portion of the second wheel partially extending through the second slot being spaced away from the second set of radial projections along the second rotational axis, the first and second set of radial projections being disposed outside the hollow tube.

\* \* \* \* \*